(12) United States Patent
Isanaka et al.

(10) Patent No.: US 10,285,938 B2
(45) Date of Patent: May 14, 2019

(54) COMPOSITION FOR THE TREATMENT OF BURNS, DIABETIC WOUNDS, OTHER TYPES OF WOUNDS AND SUBSEQUENTLY GREATLY REDUCED SCARRING

(71) Applicants: Ram Isanaka, Warren, NJ (US); Jesse Jaynes, Auburn, AL (US)

(72) Inventors: Ram Isanaka, Warren, NJ (US); Jesse Jaynes, Auburn, AL (US)

(73) Assignee: ISSAR Pharmaceutical (IN)

( * ) Notice: Subject to any disclaimer, the term of this patent is extended or adjusted under 35 U.S.C. 154(b) by 0 days.

(21) Appl. No.: 15/632,350

(22) Filed: Jun. 25, 2017

(65) Prior Publication Data

US 2017/0290770 A1 Oct. 12, 2017

Related U.S. Application Data

(62) Division of application No. 14/756,169, filed on Aug. 11, 2015, now Pat. No. 9,737,584.

(51) Int. Cl.

| | | |
|---|---|---|
| *A61K 38/08* | (2019.01) | |
| *A61K 38/00* | (2006.01) | |
| *A61K 47/02* | (2006.01) | |
| *A61K 47/06* | (2006.01) | |
| *A61K 47/10* | (2017.01) | |
| *A61K 47/12* | (2006.01) | |
| *A61K 47/14* | (2017.01) | |
| *A61K 47/24* | (2006.01) | |
| *A61K 9/06* | (2006.01) | |
| *A61Q 19/00* | (2006.01) | |
| *C07K 14/00* | (2006.01) | |
| *A61K 47/18* | (2017.01) | |
| *A61K 9/00* | (2006.01) | |

(52) U.S. Cl.
CPC ............. *A61K 9/06* (2013.01); *A61K 9/0014* (2013.01); *A61K 38/00* (2013.01); *A61K 38/08* (2013.01); *A61K 47/06* (2013.01); *A61K 47/10* (2013.01); *A61K 47/12* (2013.01); *A61K 47/14* (2013.01); *A61K 47/183* (2013.01); *A61K 47/24* (2013.01); *A61K 47/02* (2013.01)

(58) Field of Classification Search
CPC ........ A61K 38/00; A61K 38/08; A61K 47/02; A61K 47/06; A61K 47/10; A61K 47/12; A61K 47/14; A61K 47/183; A61K 47/24; A61K 9/0014; A61K 9/06; A61Q 19/00; C07K 14/00
USPC .......... 514/1.1, 21.4; 530/326, 300; 424/93.4
See application file for complete search history.

(56) References Cited

U.S. PATENT DOCUMENTS

| | | | | |
|---|---|---|---|---|
| 5,561,107 | A * | 10/1996 | Jaynes ................ | A61K 38/10 435/375 |
| 6,255,282 | B1 * | 7/2001 | Jaynes ................ | C07K 7/08 424/184.1 |
| 9,487,560 | B2 * | 11/2016 | Jaynes ................ | C07K 7/06 |
| 2002/0025918 | A1 * | 2/2002 | Jaynes ................ | C07K 7/08 514/2.8 |
| 2009/0035362 | A1 * | 2/2009 | Shih .................... | A61K 31/265 424/450 |

* cited by examiner

*Primary Examiner* — Julie Ha
(74) *Attorney, Agent, or Firm* — John Dodds; Carlos Zapatero (57) ABSTRACT

Antimicrobial peptides represent a relatively new discovery in the immune system pathway. Recent designs of synthetically engineered antimicrobial peptides have demonstrated increased potency and efficacy/tolerability, enhanced specificity, and reduced toxicity in comparison. One such peptide, XYLENTRA®, has shown/demonstrated significant promise from significant in vitro studies against a large + pathogens. Additionally, extensive animal studies have shown that the XYLENTRA® is an antimicrobial peptide against a large number of pathogens. The XYLENTRA® peptide is also solute resistant. The peptide XYLENTRA® has shown/demonstrated significant antibacterial activity on test organisms *Staphylococcus aureus* MTCC 96 and *Pseudomonas aeruginosa*. MTCC741. A substantial decrease in the microbial population level was observed in animals treated with peptide using the protocol described in detail in the application.

5 Claims, 4 Drawing Sheets

Specification includes a Sequence Listing.

COMPOSITION FOR THE TREATMENT OF BURNS, DIABETIC WOUNDS, OTHER TYPES OF WOUNDS AND SUBSEQUENTLY GREATLY REDUCED SCARRING

REFERENCE TO CROSS-RELATED APPLICATIONS:

This application is a divisional of application Ser. No. 14/756,169, filed on Aug. 11, 2015, granted as U.S. Pat. No. 9,737,584, and claims priority date of Provisional Application No. 62/070,481 filed on Aug. 26, 2014.

SEQUENCE LISTING

The instant application contains a Sequence Listing which has been filed electronically in ASCII format and is hereby incorporated by reference in its entirety. Said ASCII copy, created on Aug. 6, 2018, is named ISSAR_DIVISION-AL_SL.txt and is 751 bytes in size.

FIELD OF THE INVENTION

This invention relates to a novel composition of cream that can be used with proprietary synthetically designed bioactive peptides for the treatment of wounds. This augmented cream can be used to specifically treat burns and chronic wounds such as those found in diabetic wounds and eroded or cracked tissue particularly on the extremities. It is shown to significantly accelerate healing and protect patients from infection. Treatment of wounds with the cream also greatly reduces scarring.

BACKGROUND OF THE INVENTION

Burn Wounds

Over 1.5 million people suffer burns each year in the United States. More than 5,000 of these people will die as a direct result of the significant loss of the skin's integrity and subsequent bacterial invasion into the unprotected internal milieu of their bodies. Sepsis accounts for greater than 50% of the deaths related to patients who suffer from burns. Transmission of multi-resistant organisms to other patients, particularly in contained burn units, not only increases morbidity, but also adds an enormous cost to the healthcare system.

The current treatment of the burned patient involves fluid resuscitation, hemodynamic stabilization and the application of topical antimicrobials prior to wound excision and grafting. Bacteria flourish in dead tissue and intravenous antibiotics cannot penetrate this tissue because of its impaired blood supply. This necessitates the use of topical antimicrobials that are meant to curtail the systemic invasion of bacteria. Unfortunately, the commonly employed topical antimicrobials are often not enough to prevent the fatal consequences of burn wound sepsis. Synthetic antimicrobial peptides are specific proteins designed to encompass a greater spectrum of activity against bacteria (including multi-drug resistant organisms) and fungus than traditional topical agents.

Our proprietary peptide designs are extremely stable in hostile, non-physiologic environments. Alterations in the wound milieu, characteristics of burns, do not affect the potency or properties of the peptide making the designed peptides more effective and valuable to practitioners who manage burns, and infected or adversely colonized wounds. Sufficient promise was shown by several peptides through in vitro and in animal studies, to lead to the selection of one to be tested in several human clinical trials.

An initial double blind randomized, phase II/III clinical trial for the evaluation of a cream based peptide preparation in the topical treatment of burn wounds was conducted at Gandhi Medical College Hospital in Hyderabad, India in 2008. The mean duration to reach the total wound closure for peptide treated patients was found to be 8.4 days while the placebo group was 11.1 days. This was statistically significant at the (P<0.001). A second study consisting of 120 burn patients, begun in late 2008 was carried out at two hospitals in Hyderabad, India. In these studies the patients received no additional antibiotic therapy and none of the wounds were debrided. The final report indicated that there were no infections and significant accelerated healing with minimal scarring and the patients had significantly fewer hospital visits.

A final phase III study was recently completed utilizing a new cream composition combined with a very effective designed antimicrobial peptide. The results of this trial are found in this application.

Chronic Wounds

The loss of the skin's protective barrier as the result of unhealed wounds fosters the susceptibility to bacterial infection, invasion, and sepsis. About 40 million chronic wounds are treated globally annually. Those are wounds that get stuck in the inflammatory stage of wound healing and do not heal. Chronic wounds are the source of severe emotional and physical stress for patients and create a significant financial burden, both on patients and the whole healthcare system. In the chronic wound the balance between production and degradation of proteins is lost and degradation plays too large a role.

Chronic wounds present an enormous physical, social and economic burden worldwide and their incidence is on the rise with an aging population. It has been estimated that chronic wounds affect 120 per 100,000 people aged between 45 and 65 years and increases to 800 per 100,000 people aged over 75 year. Chronic wounds result from a number of different causes among them diabetes, pressure, atrial and venous insufficiency, vasculitis and burns. Additional complications, including infections, necrosis, tissue hypoxia, and exudates represent further challenges in dealing with a chronic wound. Poor nutrition, obesity, excessive alcohol consumption and smoking can then add an additional layer of complications to an already serious condition.

Normal wound healing progresses through three stages. The first is Inflammation that lasts 2 to 4 days from the time of injury. Upon injury hemostasis causes vascular constriction, and thrombus formation. Platelets in the wound release factors that recruit neutrophils and monocytes (macrophages), which in turn attract lymphocytes and fibroblasts to the site of injury. The proliferation stage overlaps the inflammatory stage, starts at about day 3 and lasts for several days. It is characterized by angiogenesis, collagen formation and epithelialization mediated by fibroblasts, and is complete when balance is achieved in collagen formation and its continuous breakdown by matrix metallo-proteases (MMPs). The Remodeling stage is the third and last stage and can extend over a year or more. Collagen remodeling continues, fibroblasts differentiate into myofibroblasts, vascularity decreases and tissue strength increases.

Bedsores, more properly known as pressure ulcers or decubitus ulcers, are lesions caused by many factors such as: unrelieved pressure; friction; humidity; shearing forces; temperature; age; continence and medication; to any part of the body, especially portions over bony or cartilaginous areas such as sacrum, elbows, knees, and ankles Although easily prevented and completely treatable if found early, bedsores are often fatal—even under the auspices of medical care—and are one of the leading iatrogenic causes of death reported in developed countries, second only to adverse drug reactions.

Results from a small trial utilizing a modified version of the burn cream are presented herein for the treatment of chronic wounds.

Cracked Heels

Cracked heels are a common foot problem and are often referred to as heel fissures. Cracked heels are commonly caused by dry skin (xerosis), and made more complicated if the skin around the rim of the heel is thick (callus). For most people this is a nuisance and a cosmetic problem but when the fissures or cracks are deep, they are painful to stand on and the skin can bleed—in severe cases this can become infected.

The skin is normally dry and may have a thick callus that appears as a yellow or dark brown discolored area of skin, especially along the inside border of the heel. Cracks in the skin are usually obvious.

If the cracks are severe enough, there will be pain upon weight bearing that is not there when weight is off the heel. The edges or rim around the heel will generally have a thicker area of skin (callus). Wearing open or thin-soled shoes usually make the symptoms worse.

Some people tend to have a naturally dry skin that predisposes them to the cracks. The thickened dry skin (callus) around the heel that is more likely to crack is often due to mechanical factors that increase pressures in that area.

Other factors that can be involved in the cause of cracked heels include:
  prolonged standing (at work or home, especially on hard floors)
  being overweight (this increases the pressure on the normal fat pad under the heel, causing it to expand sideways—if the skin is not supple and flexible, the pressures to 'crack' are high)
  open back on the shoes (this allows the fat under the heel to expand sideways and increases the pressure to 'crack')
  some medical conditions predispose to a drying skin (e.g. autonomic neuropathy in those with diabetes leads to less sweating; an underactive thyroid lowers the body's metabolic rate and there is a reduction in sweating, leading to a dryness of the skin)
  skin conditions (e.g. psoriasis and eczema).

Results from a small trial utilizing a modified version of the burn cream are presented herein for the treatment of cracked heels.

SUMMARY OF THE INVENTION

Background

Both the nature of the wound and microorganism-specific factors influence the rate of microbial proliferation in and penetration of the wound tissue. The wound is rich in coagulated protein and well hydrated by the trans-eschar movement of fluid and serum, creates an excellent microbial culture medium. The eschar is avascular owing to thrombosis of nutrient vessels, limiting both the delivery of systemically administered antibiotics and the migration of phagocytic cells into the burned tissue. Bacterial proliferation in the wound also can be enhanced by such factors as wound maceration, pressure necrosis, and wound desiccation with neo-eschar formation. In addition, secondary impairment of blood flow to the wound could further predispose the patient to invasive infection by curtailing the delivery of oxygen, nutrients, and phagocytic cells to the viable sub-eschar tissue.

The character of the microbial flora of the burn wound changes with time and Gram-negative organisms replace Gram-positive organisms that predominate in the early post wound period by the second week. Without the application of topical antimicrobial agents, the density of bacteria progressively increases, and the microorganisms penetrate the eschar by migration along sweat glands and hair follicles until they reach the eschar/nonviable tissue interface. If the density and invasiveness of the microorganisms exceed the host's defense capacity, proliferating organisms in the sub-eschar space can invade the underlining viable tissue, leading to invasive burn wound infection and even systemic spread to remote tissues and organs. Bacterial invasion is uncommon unless the number of microorganisms exceeds $10^5$/grams of biopsy tissue. Effective topical antimicrobial chemotherapy limits intra-eschar bacterial proliferation and the attendant risk of invasive infection.

Over the past 20 years, significant changes in the microbial ecology of the burn wound have been noted. The recovery of Pseudomonas and other gram-negative bacteria, which were once the most common organisms causing burn wound infection, has markedly declined with improvements in the isolation of patients. Patients who have received broad-spectrum antibiotics for perioperative coverage or treatment of septic complications and whose wounds remain open for many days owing to the extent of the burn are at increased risk of burn wound colonization and infection by yeasts, fungi, and multiple antibiotic-resistant bacteria. The true fungi have replaced bacteria as the most common microbes causing burn wound infection in recent years. *Pseudomonas aeruginosa, Staphylococcus aureus* and *Aspergillus* species are the commonest organisms associated with burn wound infection.

Mafenide acetate, 1% SSD and silver nitrate are the three most commonly employed topical antimicrobial agents for burn wound care. Each agent has specific limitations and advantages.

1% SSD burn cream is most effective when applied to burns soon after injury to minimize bacterial proliferation on the wound's surface. It has limited solubility in water and, therefore, limited ability to penetrate into the eschar. With continual use, resistance to the sulfonamide component of 1% SSD is common, particularly in certain strains of *Pseudomonas* and many *Enterobacter* species. Mafenide acetate diffuses freely into the eschar owing to its high degree of water solubility. It is the preferred agent if the patient has heavily contaminated burn wounds or has had burn wound care delayed by several days. Hypersensitivity reactions occur in 7% of patients. This agent also inhibits carbonic anhydrase, and a diuresis of bicarbonate often is observed after its use. The resultant metabolic acidosis could accentuate post-burn hyperventilation, and significant acidemia could develop if compensatory hyperventilation is impaired. A 0.5% silver nitrate solution has a broad spectrum of antibacterial activity imparted by the silver ion. This agent does not penetrate the eschar because the silver ions are rapidly precipitated on contact with any protein or cationic material.

It is clear that the topical agents are crucial in the ultimate eradication of the burn and infected wound pathogens since it is extremely difficult to administer the intravenous antibiotics to non-perfused tissue such as burned skin. The poorly vascularized, wounded skin is, therefore, the portal of entry and the ongoing nidus of infection for burn victims. The ideal topical agent should be highly active against common and multi-resistant pathogens, such as methicillin resistant *Staphylococcus aureus*, vancomycin resistant *Enterococcus faecium/faecalis*, and extended spectrum β-lactamase producing Gram- negative organisms, while having a neutral or even beneficial effect on the wound healing process.

Antimicrobial peptides represent a relatively new discovery in the immune system path-way. These small peptides are inducible elements of the immune system that serve as nonspecific effector molecules to eradicate infection caused by bacteria, yeast, and viruses, protecting host epithelial surfaces such as the tracheal mucous membrane and genitourinary tract. In mammals, several of these compounds are known to be present in high concentrations in neutrophilic granules and phagocyte vacuoles. These peptides differ significantly in their structure between species but, in common, appear to create amphipathic helical or beta-pleated structures. The mechanism of action is different from currently utilized antibiotics and appears to be based on their ability to insert into membranes, from channels or "pores", and destroy the cell by changing membrane conductance and altering intracellular function. Based upon the principles discovered in naturally occurring peptides, recent designs of synthetically engineered antimicrobial peptides have demonstrated increased potency and efficacy/tolerability, enhanced specificity, and reduced toxicity in comparison. These peptides termed as designed antimicrobial peptides (dAMP), are resistant to such effects of high solute levels and demonstrate even greater antibacterial activity.

One such peptide, XYLENTRA®, has showed significant promise from significant in vitro studies against a large number of pathogens through to extensive animal studies and is very solute resistant. These types of antimicrobial peptides show enormous promise in treating patients with chronic wounds or burn wound sepsis. The impact of this would improve patient survival or quality of life and reduce costs to the patient, their family, hospital and society.

The peptide XYLENTRA® showed significant antibacterial activity on test organisms *Staphylococcus aureus* MTCC 96and *Pseudomonas aeruginosa* MTCC 741. The test compound showed 100% killing of *Staphylococcus aureus* on exposure to 1 µM (4.3 µg/ml) and 5 µM (21.5 µg/ml) concentrations for 1 hr at pH 7.2, and at pH 8.4 an exposure of 4 hrs was required to get 100% killing. Whereas, 100% killing of *Pseudomonas aeroginosa* was observed on exposure to the test compound for 1 hr at pH 8.4 and an exposure of 4 hrs was required for 100% killing at pH 7.2.

The microbiological studies with XYLENTRA® in vivo using a rat burn wound model were conducted. The observations on the bacterial growth in eschar and sub-eschar muscles on post burn day one, two or three in peptide treated and control treated groups were made. A substantial decrease in the microbial population level was observed in animals treated with peptide.

Subacute toxicity studies of XYLENTRA® in rats and rabbits demonstrated that it was safe. No abnormalities in physical, physiological, biochemical and histo-pathological parameters were observed on application of the peptide. No mortality was seen in animals from any group. There is evidence (dermal histopathology findings) to show that XYLENTRA® has stimulatory action on tissue growth (increased collagen content in granulation tissue and re-epithelialization) thus promoting improved wound healing (unpublished observations).

The results of a Phase-I clinical trial (n=24) on healthy human patients revealed that XYLENTRA® cream administered topically twice a day was safe. There was an absence of any symptoms or signs of toxicity at the evaluation site and considered a measure of primary efficacy/tolerability was established in this study. XYLENTRA® was safe and adverse events were found to be minimal in tire Phase-I Study. Mild redness and itching was seen in 2/24 volunteers. Treatment Groups (2% and 4%) were similar in efficacy/tolerability and safety parameters studied. Pharmacokinetic data was analyzed by HPLC at different time intervals and suggested no systemic absorption of the drug.

It was demonstrated in a phase II study (n=120) with the XYLENTRA® Peptide Treatment Groups (0.02% & 0.05%) dial the incidence rate of wound healing was better in terms of time to complete wound healing and achievement of a superior overall wound evaluation score over the Placebo Group. Scar formation was also significantly lower compared to that in Placebo Group, indicating that treatment with XYLENTRA® enabled more complete healing with less morbidity. It is safe and highly effective in promoting burn wound healing for patients with partial thickness burns that are less than or equal to 20% without any side effects. None of the XYLENTRA® treated volunteers developed any adverse reaction. Pharmacokinetic data suggested the absence of systemic absorption.

Description of XYLENTRA®
Description of Xylentra

The proprietary cream mixture proven to be efficacious in treating burn, chronic and cracked heel wounds is composed of a sufficient amount of the peptide:

FAKKFAKKFAKFAKKFAKFAFAF (SEQ ID NO:1) and a cream with the following composition found in Table 1.

Results of Phase III Burn Trial
Study Objective

To compare safety and efficacy of 1% SSD with XYLENTRA® in patients with partial thickness burns in India.

In India about 60,000 people suffer from burns annually, more than 50,000 are treated in hospitals and about 10,000 succumb to thermal injury. Exact figures are likely to be even higher, considering the poverty, illiteracy, poor standards of safety at home and industry. Thus the burn 'disease' is endemic in India. House and structuale fires are responsible for >70% of the yearly 3,785 burn-related deaths, 75% of which result from smoke inhalation or asphyxiation and 25% are due to burns. Injuries due to contact with flame or ignition of clothing are the most common cause of burn in adults whereas scald burns are most common in children. The majority of patients sustain burns of such limited severity and extent (>80% of burns involve <20% of the body surface) that they can be treated on an outpatient basis. Approximately 33% of patients who require in-hospital care have a major burn injury as defined by the American Burn Association on the basis of burn size, causative agent, and associated injuries and should be treated in a tertiary care burn center.

Study Population

Patients of either gender with partial thickness burns referred to a tertiary referral center Number of Subjects Enrolled: 160

Methodology
1. Study Design
    a. Multi-center, double-blind, randomized parallel design study in 200 patients of partial thickness burns
2. Study Period
    a. 12 months 3. Study Procedure
   a. Participants satisfying the inclusion criteria were hospitalized for the study duration and were randomized in a 1:1 ratio to receive either SSD 1% or XYLENTRA®. Randomization was done specific for each center. Allocation concealment was maintained. The drugs were topically administered once daily for 4 weeks or until complete wound healing, whichever was earlier. The patients were discharged only after complete healing of wound and recovery from other secondary effects of burns. A follow up was done on the 3$^{rd}$ month to record the frequency of scars[10], keloids or contracture formation.
   b. Key Criteria for Inclusion/Exclusion:
      i. Inclusion:
         1. Either sex
         2. Age 18-60 years
         3. Those diagnosed with partial thickness thermal burns as per clinically
         4. Total surface area of the burn 10-20% as per Wallace rule of nine
         5. Willing to give written informed consent.
         6. Females of child-bearing potential with a negative urine pregnancy test on Day 1
         7. Weight range within 20% of the ideal body weight as per standard tables and Indian criteria
      ii. Exclusion:
         1. History of intercurrent illnesses
         2. History of drug addiction
         3. History of chronic GI, renal, hepatic, respiratory, infectious, or History of allergy or hypersensitivity to investigational drugs
         4. Chronic smokers and/or history
         5. Patients with pulmonary burn
         6. Patients with chemical or electrical burns
         7. Patients taking any antibiotics Investigational Product
  XYLENTRA®
Dose
  4 gms/1% burn
Mode of Administration
  Topical
Duration of Treatment
  For 4 weeks or till the day of complete wound healing whichever was earlier.
Criteria for Evaluation
  Primary variable
  1. Proportion of patients having complete closure/healing of the wounds during 28 days
     a. Time points to measure endpoint:
        1, 4, 6, 8, 10, 12, 14, 16, 18, 20, 22, 24, 26 and 28±1 days
  Primary variable
  2. Proportion of patient with controlled secondary infection during 28 days
     a. Time points to measure endpoint:
        1, 4, 8, 12, 16, 20, 24 and 28±1 days
  Secondary variables
  1. Extent of non-viable tissue by clinical evaluation % of wound covered with non-viable tissue (clinically)
     76-100%
     51-75%
     26-50%
     1-25%
     No Necrotic Tissue
  2. Degree of granulation by visual Score % of wound filled with granulation tissue (clinically)
     No Granulation
     Scanty Granulation
     Healthy Granulation
  3. Wound Evaluation Done on Four Parameters (clinically):
     Erythema (redness of the skin caused by dilatation and congestion of the capillaries, often a sign of inflammation or infection)
     Edema (excessive accumulation of serous fluid in tissue spaces)
     Purulence (the state or condition of containing or secreting pus)
     Necrotic Tissue (dead, devitalized tissue)
  Each of these parameters is measured on a scale of 0-3 as follows:
     0=Absent; 1=Mild; 2=Moderate; 3=Severe.
  4. Complete closure/healing of the wound (clinically). [Time Frame (in days): Admission to burn unit to 100% wound healing]
     a. Time points to measure secondary endpoint: 1, 4, 6, 8, 10, 12, 14, 16, 18, 20, 22, 24, 26 and 28±1 days.

Safety
  Safety was measured by pretreatment and post treatment biochemical investigations (Hematological variables) and physical examination. Subjects were thoroughly monitored for adverse effects.

Conclusions
  One hundred and sixty patients completed the study. The objective was to compare the safety and efficacy of XYLENTRA® with Silver Sulfadiazine in patients with partial thickness burns. The patients were topically administered with either XYLENTRA® or Silver Sulfadiazine cream based on allocation concealment once daily for 4 weeks or until complete wound healing whichever is earlier.

The study met its primary endpoints. The proportion of patients with complete wound closure, was statistically significant between the XYLENTRA® and Silver Sulfadiazine group. The patients with complete wound closure were 75 (94%) (N=80) and 65 (81%) (N=80) in the XYLENTRA® and Silver Sulfadiazine groups, respectively in the four week time period. Moreover, XYLENTRA® demonstrated accelerated healing rates when compared to Silver Sulfadiazine. The time taken for complete wound closure was found to be less in Xylentra group compared to Silver Sulfadiazine group as more number of patients had complete wound closure at various time points in the XYLENTRA® group when comparison to the Silver Sulfadiazine group. Cumulative wound healing was found to be better in XYLENTRA® group when compared to Silver Sulfadiazine group. Cumulative wound healing was 85.42% XYLENTRA® group and 78.71% in Silver Sulfadiazine.

Burn wounds are a richer source of infection than surgical wounds, primarily because of the larger area involved and longer duration of patient stay in the hospital, in this study, clinical and statistically significant differences were found in the proportion of patients with controlled secondary infections between the groups. XYLENTRA® showed increased efficacy in controlling the infection rate as evident front 41.7% of patients with controlled secondary infection in the XYLENTRA® group when compared to 25% of patients with controlled secondary infection in Silver Sulfadiazine group. Additionally, antibiotic usage was lower by patients in the XYLENTRA® group when compared to the Silver Sulfadiazine group.

Most commonly encountered and clinically significant impediments to wound healing are the presence of non-viable tissue and granulation. XYLENTRA® proved to be efficacious in controlling both non-viable tissue and granulation throughout the study period. Both the evaluation of mean score of non-viable tissue and patient wise evaluation confirmed that XYLENTRA® remarkably reduced non-viable tissue and granulation in comparison to Silver Sulfadiazine. On study termination day, no non-viable tissue was found in 78 (97.50%) and 71 patients (88.75%) in XYLENTRA® and Silver Sulfadiazine groups, respectively. It was clinically observed that non-viable tissue became necrotic tissue in the Silver Sulfadiazine treated patients. However non-viable tissue appeared during the initial visits in XYLENTRA® treated patients but no necrotic tissue was observed during the study period. Similarly, at the end of study termination day, the number of patients observed with no granulation in XYLENTRA® group was 75 (93.75%) and 63 (78.75%) in the Silver Sulfadiazine group.

XYLENTRA® also proved to be potent in wound evaluation based on clinical parameters. It was effective in controlling edema, erythema and purulence as evident from the results of mean score analysis and patient wise analysis. Patients with no edema, no erythema and no purulence were found to be less in number in XYLENTRA® group when compared to Silver Sulfadiazine group. On study termination day, no erythema was found in 78 (97.50%) and 74 patients (92.50%) in XYLENTRA® and Silver Sulfadiazine groups respectively. No edema was found in 79 (98.75%) and 74 (92.50%) in XYLENTRA® and Silver Sulfadiazine groups, respectively. No purulence was found in 78 (97.50%) and 74 (92.50%) patients in XYLENTRA® and Silver Sulfadiazine groups, respectively. In addition, the mean scores of erythema, edema and purulence were found to be considerably lower in XYLENTRA® group in comparison to Silver Sulfadiazine group. In addition to these primary efficacy and secondary efficacy endpoints, other variables that demonstrate the potency of the drug such as drug's ability to reduce scar (pigmentation and thickness), itching and breaking were evaluated. Scar maturation and normal skin formation always will be depending on the quality of wound healing. Patients of post-burn contractures, scars defects and disfigurements constitute almost half of the workload of many general plastic surgeons; especially this will directly increase the cost to patient for surgical procedures. Hence choosing the quality healing medicine is very important step in burn wound management. The clinical observations showed that most of the XYLENTRA® treated patients' wound area returned to their normal skin color without any scar or contracture formation. However, most of the patients treated with Silver Sulfadiazine had dark pigmentation with hypertrophic scars with contractures. Hyper pigmentation and hypo pigmentation was significantly less in XYLENTRA® group (13% and 16%) when compared to Silver Sulfadiazine group (25% and 21%). The area with paper thin and hypertrophic scar was more than twice in Silver Sulfadiazine group (6% and 25%) when compared to XYLENTRA® group (2% and 12%). Itching was found significantly greater in treated patients (51%) in Silver Sulfadiazine group in comparison to XYLENTRA® group (14%). In addition, 18% of treated patients in Silver Sulfadiazine group had breaking of skin in comparison to 3% of treated patients in XYLENTRA®. These results demonstrate the fact that XYLENTRA® has the ability to heal the wound effectively and controlling the development of scars, pigmentation, itching and breaking.

The treatment emergent adverse events (TEAEs) observed were mostly skin related disorders. All the adverse events were found to be mild in nature. No serious adverse events and no deaths were reported in the study. The adverse events frequently experienced by patients in the study were swelling, irritation, itching, redness and pain. All these adverse events were observed in high percentage of patients and were present for longer duration in Silver Sulfadiazine group when compared to XYLENTRA® group.

Burn Wounds

A summary of the statistical measurements of the test variables is listed in Table 2.

Figure 1A:
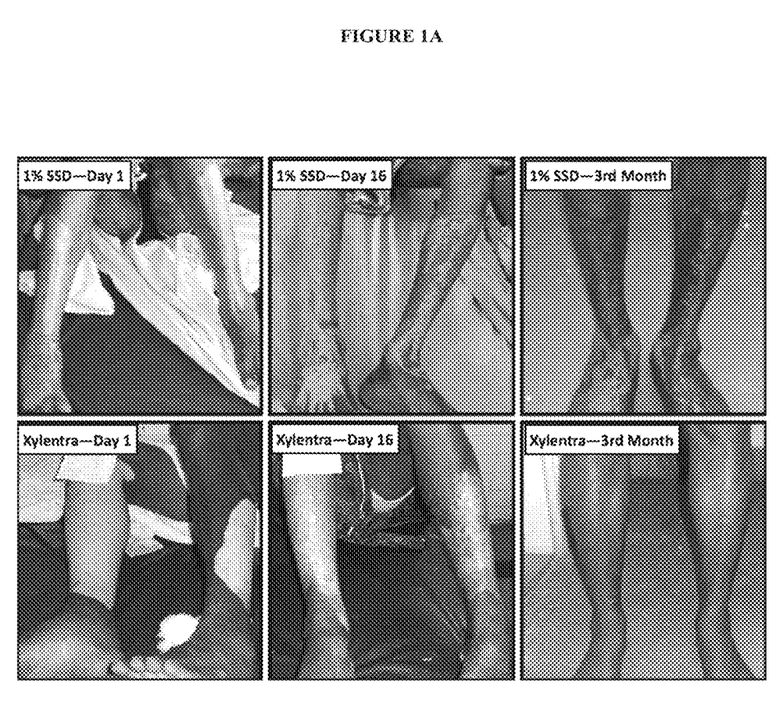
FIG. 1A and FIG. 1B—Photographic comparison of burn treatments can be found in both FIG. 1A and FIG. 1B.
Figure 1B:
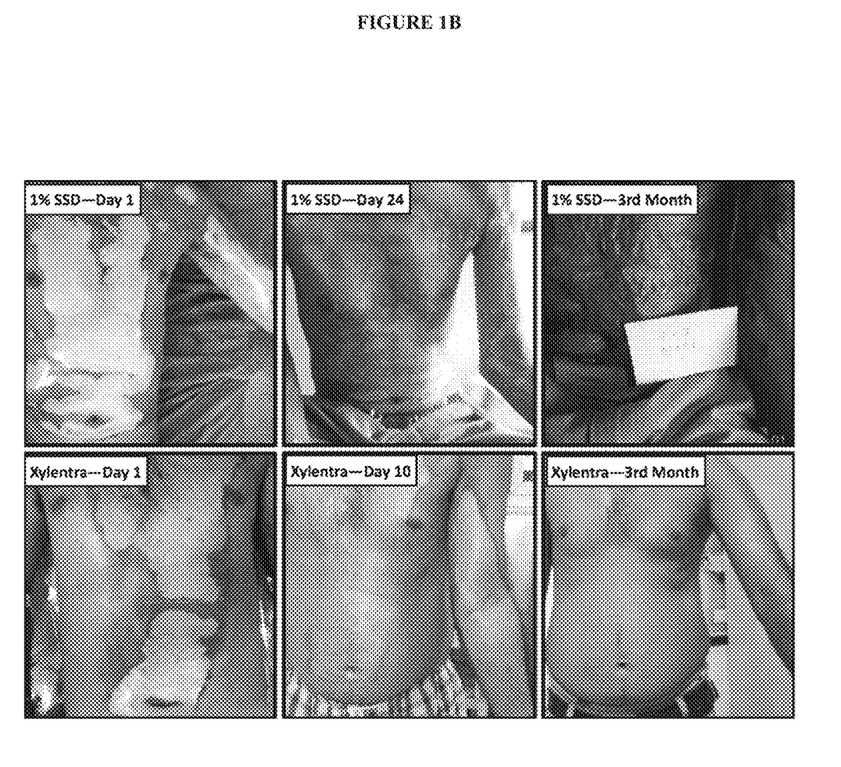

Photographic comparison of both treatments can be found in FIGS. 1A and B.

Diabetic Wound Experiments

Figure 2:
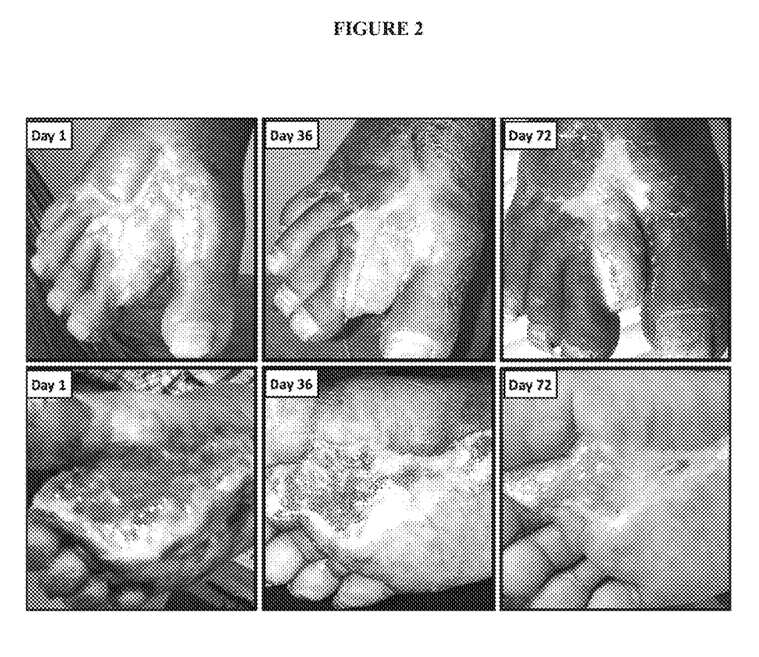
FIG. 2. Patients were treated with the XYLENTRA® cream once per day for the indicated times listed in the Figure.

Patients were treated with the XYLENTRA® cream once per day for the indicated times listed on FIG. 2.

Other Types of Chronic Wounds:

Cracked Feet Experiments

Figure 3:
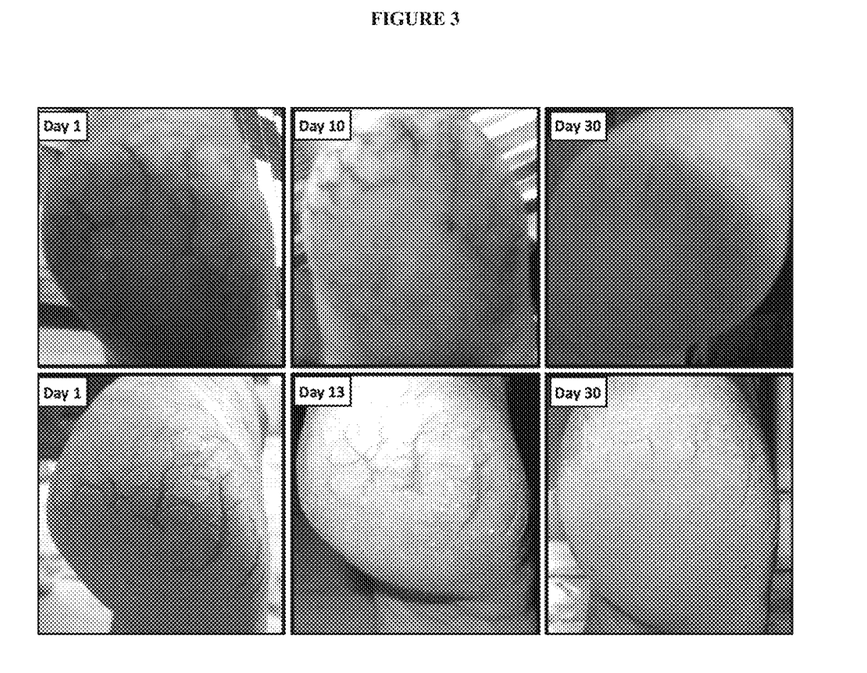
FIG. 3. Patients were treated with the XYLENTRA® cream once per day for the indicated times listed in the Figure.

Patients were treated with the XYLENTRA® cream once per day for the indicated times listed on FIG. 3.

TABLE 1

Composition of Cream

| | | |
|---|---|---|
| 1 | Cetomacrogol-1000 | 2-5% |
| 2 | Stearyl Alcohol | 8-15% |
| 3 | Liquid Paraffin | 3-6% |
| 4 | White Petroleum Jelly | 15-20% |
| 5 | Propylene Glycol | 6-10% |
| 6 | Peptide | 0.05-2.0% |
| 7 | Sodium Methyl Paraben | 0.1-0.2% |
| 8 | Sodium Propyl Paraben | 0.05-0.1% |
| 9 | Sodium Phosphate | 0.1-0.3% |
| 10 | Sodium Acid Phosphate | 0.01-0.03% |
| 11 | EDTA Disodium | 0.01-0.03% |
| 12 | Citric Acid | 0.3-0.8% |
| 13 | Purified Water | 50-65% |

TABLE 2

Summary of Statistical Measurements of Test Variables

| | p-value | Significant |
|---|---|---|
| Primary Variables | | |
| Variable 1 | | |
| % Patients achieving complete wound closure/healing | 0.005 | YES |
| Variable 2 | | |
| % Patients with controlled secondary infections | 0.017 | YES |

TABLE 2-continued

Summary of Statistical Measurements of Test Variables

|  | p-value | Significant |
|---|---|---|
| Secondary Variables | | |
| Variable 1 | | |
| % of wound covered with non-viable tissue | <0.001 | YES |
| Variable 2 | | |
| Degree of granulation | 0.026 | YES |
| Variable 3 | | |
| Erythema | 0.310 | NO |
| Edema | 0.204 | NO |
| Purulence | 0.019 | YES |
| Necrotic Tissue | 0.035 | YES |
| Variable 4 | | |
| Time to achieve complete closure/wound healing | <0.0001 | YES |
| Additional Variables | | |
| Scarring | | |
| % Normal Skin | <0.001 | YES |
| % Hypertrophic Scar | 0.005 | YES |
| % Paper Thin Scar | 0.027 | YES |
| % Raw Area | 0.136 | NO |
| % Itching | 0.001 | YES |
| % Breakdown of Skin | 0.006 | YES |
| % Normal Pigmentation | <0.001 | YES |
| % Hyper Pigmented Scar | 0.004 | YES |
| % Hypo Pigmented Scar | 0.066 | NO |
| % Mottled Scar | 0.470 | NO |

The invention claimed is:

1. A method of treating a wound, which comprises:
   administering to the wound a therapeutically effective dose of a composition comprising an antimicrobial peptide,
   wherein the antimicrobial peptide comprises SEQ ID NO:1,
   thereby yielding significant reduction in scarring caused from wounds.

2. The method of claim 1, wherein the wound is a burn.

3. The method of claim 1, wherein the wound is a diabetic wound.

4. The method of claim 1, wherein the antimicrobial peptide exhibits antimicrobial activity on *Staphylococcus aureus* and *Pseudomonas aeruginosa*.

5. The method of claim 1, wherein the composition is in the form of a cream.

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Ala Lys Lys Phe Ala Lys Lys Phe Ala Lys Phe Ala Lys Lys Phe
1               5                   10                  15

Ala Lys Phe Ala Phe Ala Phe
            20
```